(12) United States Patent
Hagemeister et al.

(10) Patent No.: US 7,629,303 B2
(45) Date of Patent: Dec. 8, 2009

(54) FLUIDS HAVING PARTIALLY HYDROGENATED SUBSTITUTED STYRENE LINEAR DIMERS AND METHOD OF MAKING SAME

(75) Inventors: Mark Paul Hagemeister, Montville, NJ (US); Thomas R. Forbus, Jr., Lexington, KY (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 798 days.

(21) Appl. No.: 11/205,679

(22) Filed: Aug. 17, 2005

(65) Prior Publication Data
US 2006/0069212 A1    Mar. 30, 2006

Related U.S. Application Data

(60) Provisional application No. 60/602,367, filed on Aug. 18, 2004.

(51) Int. Cl.
*C10M 127/04* (2006.01)
*C07C 2/72* (2006.01)

(52) U.S. Cl. .................................. 508/591; 585/428
(58) Field of Classification Search ................ 508/591; 585/428
See application file for complete search history.

(56) References Cited

U.S. PATENT DOCUMENTS 3,925,217 A    12/1975    Green et al. ............. 252/52 A
3,994,816 A    11/1976    Wygant .................. 252/73

FOREIGN PATENT DOCUMENTS

| GB | 1 530 430 | | 1/1978 |
| GB | 1530430 A | * | 11/1978 |
| JP | 48044240 A | * | 9/1974 |
| JP | 09227888 | | 2/1997 |
| JP | 09227888 A | * | 9/1997 |

OTHER PUBLICATIONS

Chaudhuri, B., and Sharma, M.M., Ind. Eng. Res. 1989, 28(12), 1757-1763.*

* cited by examiner

*Primary Examiner*—Glenn Caldarola
*Assistant Examiner*—Jim Goloboy
(74) *Attorney, Agent, or Firm*—Andrew B. Griffis; Nancy T. Krawczyk

(57) ABSTRACT

A basestock that comprises a fully hydrogenated substituted styrene linear dimer; a partially hydrogenated mono-aromatic substituted styrene linear dimer; and a partially hydrogenated di-aromatic substituted styrene linear dimer. A process of producing a basestock that comprises reacting a feed stream that comprises substituted styrene, alcohol, and a dimerization catalyst, in the presence of a solvent, to form a crude slurry of dimerized substituted styrene; and partially hydrogenating the dimerized substituted styrene with hydrogen over a Group VIII catalyst to form a basestock that comprises a fully hydrogenated substituted styrene linear dimer and a partially hydrogenated substituted styrene linear dimer.

28 Claims, 1 Drawing Sheet

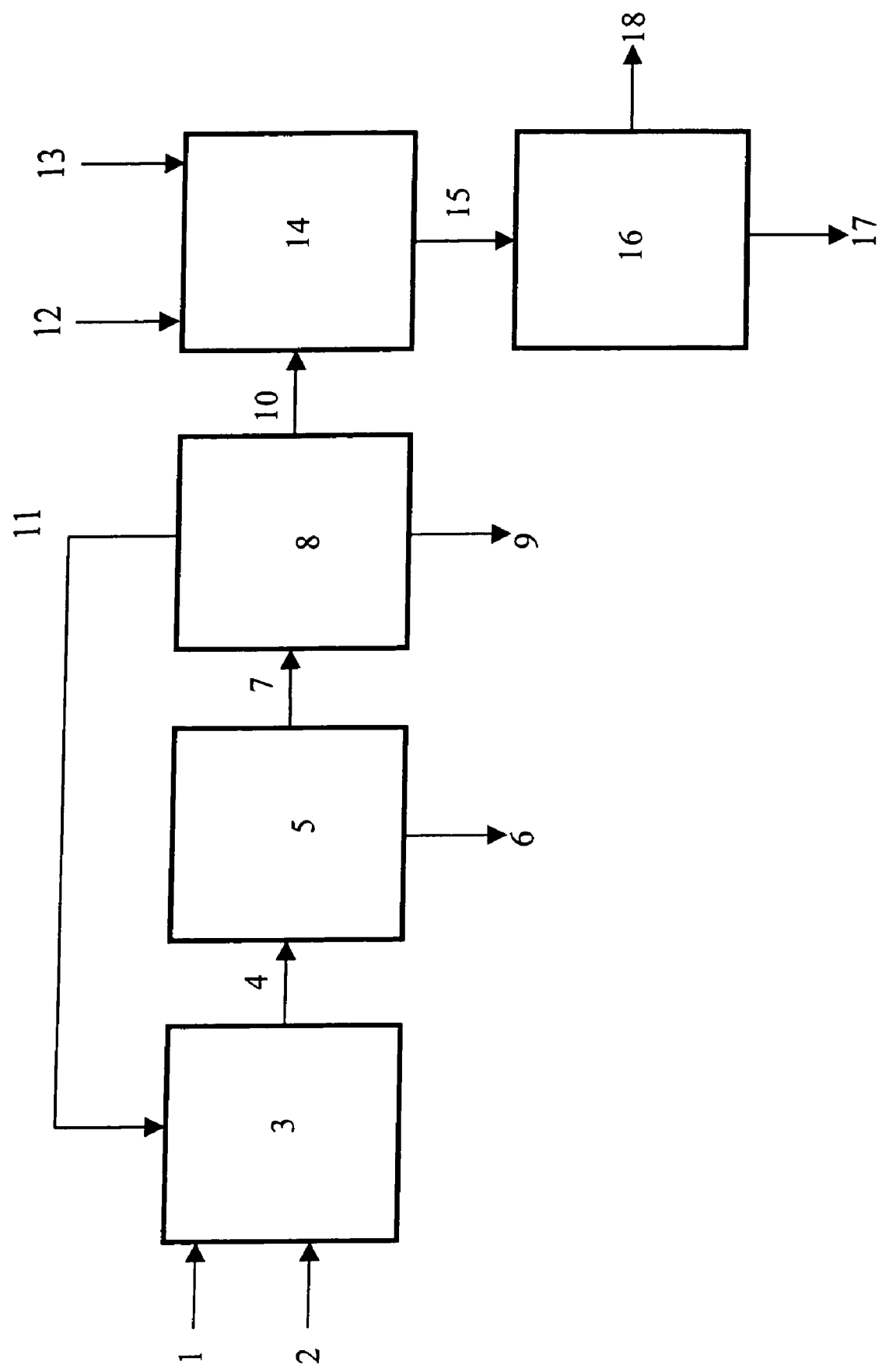

FLUIDS HAVING PARTIALLY HYDROGENATED SUBSTITUTED STYRENE LINEAR DIMERS AND METHOD OF MAKING SAME

CROSS-REFERENCE TO RELATED APPLICATIONS

This application claims the benefit of U.S. Provisional Application Ser. No. 60/602,367, filed Aug. 18, 2004, the disclosure of which is fully incorporated herein by reference.

FIELD OF THE INVENTION

The present invention relates to fluids having lubricating properties and more particularly to fluids comprising partially hydrogenated substituted styrene linear dimers, methods of making the same and their use as lubricants.

BACKGROUND

New vehicular power transmission technologies, such as infinitely variable transmissions (IVTs) and traction drives, are currently being developed based upon torque transmission between smooth rolling elements. These new transmissions require lubrication between the rolling elements, and torque is actually transmitted through the lubricant film. Therefore, the shear strength properties of the lubricant under the high shear stress conditions of the contacts govern the level of power throughput capability and efficiency. Thus lubricants with high elastohydrodynamic shear strength are required for these applications but equally, as in normal geared transmissions, it is preferable for the lubricants to exhibit low dependence of viscosity on temperature (high Viscosity Index) and good low temperature viscometrics.

However, fluids that have high elastohydrodynamic shear strength have generally been found to have poor temperature-viscosity behavior and poor low temperature viscometric properties. This is due to the fact that the structural features of fluids that impart high shear strength generally also impart poor temperature-viscosity behavior, both in terms of low temperature dynamic viscosity and Viscosity Index (VI). Thus, few lubricants are currently marketed as being suitable for use in IVT's and these are not only very expensive but they tend to have such poor temperature-viscosity properties, especially at low temperatures, as to be considered inadequate for IVT fluid application in many parts of the world, including the United States of America.

There is therefore a need for fluids that combine good high pressure shear strength properties with good temperature-viscosity properties.

According to the invention, it has been found that combining certain diphenyl-, phenylcyclohexyl- and bis-cyclohexyl-alkane fluids, mixed fluids are obtained that have high elastohydrodynamic shear strength and improved temperature-viscosity behavior.

It is known from, for example, U.S. Pat. No. 3,994,816 that power in a hydraulic transmission system can be transmitted by a synthetic fluid comprising substantially completely hydrogenated dimers of alpha-alkyl styrenes, such as 2,4-dicyclohexyl-2-methylpentane. In particular, the synthetic fluid composition disclosed in the '816 patent comprises a major amount of hydrogenated dimers of α-methylstyrene having less than about 2% unsaturation, the fully hydrogenated dimer consisting essentially of at least about 80% by weight of fully hydrogenated dimer of a linear dimer and from 0% to 20% by weight of fully hydrogenated dimer of a cyclic dimer. However, although 2,4-dicyclohexyl-2-methylpentane exhibits high elastohydrodynamic shear strength, its temperature-viscosity properties are very poor.

Japanese Kokai Patent Application No. 09-227888A discloses a fluid for a traction drive having increased oxidation resistance and comprising (a) 0.5 to 20 weight %: of one or more of the following hydrocarbons: 2-methyl-2,4-diphenylpentane; 2-methyl-4-cyclohexyl-2-phenylpentane; 2-methyl-2-cyclohexyl-4-phenylpentane; 2,4-dimethyl-2,4,6-triphenylheptane; 2,4-dimethyl-2-cyclohexyl-4,6-diphenylheptane; 2,4-dimethyl-4-cyclohexyl-2,6-diphenylheptane; 2,4-dimethyl-6-cyclohexyl-2,4-diphenylheptane; 2,4-dimethyl-4,6-dicyclohexyl-2-phenylheptane; 2,4-dimethyl-2,6-dicyclohexyl-4-phenylheptane; and 2,4-dimethyl-2,4-dicyclohexyl-6-phenylheptane, with the balance consisting of a base material of a fluid commonly used for traction drive, including, for example, hydrides of dimers or trimers of α-methylstyrene, such as 2-methy-2,4-dicyclohexylpentane; 2-methyl-2,4-dicyclohexylbutane; 2,4-dimethyl-2,4,6-tricyclohexylheptane; hydrides of indan compounds formed from dimers of α-methylstyrene, hydrides of dimers through hexamers of cyclopentadiene that may also be alkylated, and alkylated decalin compounds, such as trimethyl decalin and isopropyl decalin. The hydrocarbons (a) may be produced by the partial hydrogenation of the dimers and trimers of α-methylstyrene.

SUMMARY OF THE INVENTION

In one aspect, the present invention resides in a basestock comprising (i) from about 10 weight % to about 78 weight % fully hydrogenated substituted styrene linear dimer; (ii) from about 10 weight % to about 60 weight % partially hydrogenated mono-aromatic substituted styrene linear dimer; and (iii) from about 0 weight % to about 30 weight % partially hydrogenated di-aromatic substituted styrene linear dimer, wherein the weight % is based on the total of (i), (ii) and (iii).

Conveniently, the basestock comprises (i) from about 35 weight % to about 62 weight %, such as from about 40 weight % to about 50 weight %, fully hydrogenated substituted styrene linear dimer; (ii) from about 32 weight % to about 53 weight %, such as from about 38 weight % to about 48 weight %, partially hydrogenated mono-aromatic substituted styrene linear dimer; and (iii) from about 3 weight % to about 10 weight %, such as from about 7 weight % to about 9 weight %, partially hydrogenated di-aromatic substituted styrene linear dimer, wherein the weight % is based on the total of (i), (ii) and (iii).

One embodiment of the present invention provides a process of producing a basestock, the process comprising (i) reacting a feed stream comprising from about 96 weight % to about 98 weight % substituted styrene, from about 1 weight % to about 2 weight % alcohol, and from about 1 weight % to about 2 weight % dimerization catalyst, in the presence of a solvent, wherein the weight % is based on the total weight of the substituted styrene, alcohol, and dimerization catalyst, to form a crude slurry of dimerized substituted styrene; and (ii) partially hydrogenating the dimerized substituted styrene with hydrogen over a Group VIII catalyst to form a basestock comprising (i) from about 10 weight % to about 78 weight % fully hydrogenated substituted styrene linear dimer; (ii) from about 10 weight % to about 60 weight % partially hydrogenated mono-aromatic substituted styrene linear dimer; and (iii) from about 0 weight % to about 30 weight % partially hydrogenated di-aromatic substituted styrene linear dimer, wherein the weight % is based on the total weight of the basestock.

One embodiment of the present invention provides a basestock comprising (i) from about 35 weight % to about 65 weight % 2,4-bis-cyclohexyl-2-methylpentane; (ii) from about 30 weight % to about 55 weight % 2-phenyl-4-cyclohexyl-2-methylpentane and 2-cyclohexyl-4-phenyl-2-methylpentane; and (iii) from about 5 weight % to about 15 weight % 2,4-diphenyl-2-methylpentane, wherein the weight % is based on the total of i, ii and iii.

BRIEF DESCRIPTION OF THE DRAWINGS

FIG. 1 shows one embodiment of a process for producing hydrogenated substituted styrene linear dimers.

DETAILED DESCRIPTION OF THE INVENTION

The present invention is directed to a basestock comprising fully and partially hydrogenated substituted styrene linear dimers, and to a process for producing such a basestock.

As used herein the term "fully hydrogenated" means no remaining olefinic or aromatic unsaturation, whereas the term "partially hydrogenated di-aromatic" refers to compounds wherein only the olefinic unsaturation is hydrogenated and the term "partially hydrogenated mono-aromatic" refers to compounds wherein the olefinic unsaturation is hydrogenated and one aromatic ring is hydrogenated.

The difference in the degree of hydrogenation of the various components of the basestock of the invention is illustrated by the dimerization and hydrogenation products of alpha-methylstyrene shown in Formulae I to VII below:

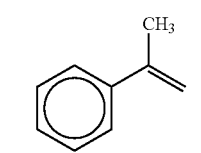
(I)

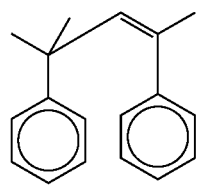
(II)

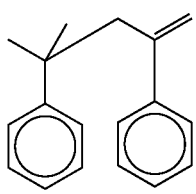
(III)

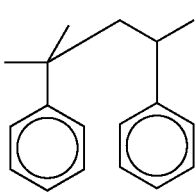
(IV)

-continued

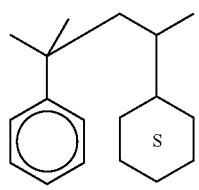
(V)

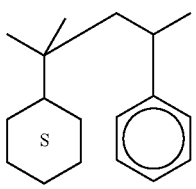
(VI)

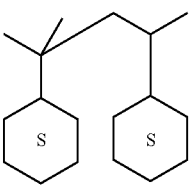
(VII)

Thus the acid catalyzed dimerization of alpha-methylstyrene (I) forms primarily two dimers, 2-methyl-2,4-diphenylpent-3-ene (II) and/or the 2-methyl-2,4-diphenylpent-1-ene (III) that have both olefinic unsaturation and aromatic unsaturation. The mixture of olefinic, di-aromatic dimers II and III can then be partially hydrogenated to form a mixture of partially hydrogenated dimers, IV (di-aromatic), V (mono-aromatic) and VI (mono-aromatic) and fully hydrogenated VII. Partially hydrogenated di-aromatic dimer IV is formed from both II and III when only the olefinic unsaturation is hydrogenated. Additional hydrogenation of the partially hydrogenated, unsymmetrical di-aromatic dimer IV produces two partially hydrogenated mono-aromatic dimers V and VI. The partially hydrogenated mono-aromatic dimer V is produced when the 4-phenyl group of IV is hydrogenated to form a cyclohexyl group, but the 2-phenyl group remains unhydrogenated. The partially hydrogenated mono-aromatic dimer VI is produced when the 2-phenyl group of IV is hydrogenated to form a cyclohexyl group, but the 4-phenyl group remains unhydrogenated. The fully hydrogenated (no remaining olefinic or aromatic unsaturation) VII is formed when both the 2-phenyl and the 4-phenyl group in IV are hydrogenated to form 2-cyclohexyl and 4-cyclohexyl groups.

The acid catalyzed dimerization of I also may form a cyclic dimer VIII, not shown in drawings, which may also be partially or fully hydrogenated, in a manner analogous to that described above for dimers II and III.

In a similar manner, the acid catalyzed dimerization of beta-methylstyrene could form a mixture primarily of isomers of 3,4-diphenylhexenes. Partial hydrogenation would effect the reduction of (1) the olefinic unsaturation or (2) the olefinic unsaturation and one of the two phenyl groups. Full hydrogenation would effect the reduction of the olefinic unsaturation and both of the phenyl groups.

Basestock

The American Petroleum Institute defines five groups of basestocks labeled Groups I to V respectively. Groups I, II and III basestocks are mineral oils classified by the amount of saturates and sulfur they contain and by their viscosity indices. Group I basestocks are solvent refined mineral oils. They contain less saturates, more sulfur and may have lower viscosity indices. They define the bottom tier of lubricant performance. Group I basestocks are the least expensive to produce and currently account for about 75 percent of all basestocks. These comprise the bulk of "conventional" basestocks.

Groups II and III basestocks are high viscosity index and very high viscosity index basestocks. They are hydroprocessed mineral oils with higher saturates and lower sulfur than Group I basestocks. The Group III oils contain less saturates and sulfur than the Group II oils and have higher viscosity indices than both the Group II or Group I oils. Groups II and III basestocks provide better performance than the Group I basestocks, particularly in terms of their thermal and oxidative stability. Isodewaxed oils also belong to Groups II and III basestocks, with the isomerization dewaxing removing a significant portion of the waxes contained by the oils and thereby improving their cold temperature performance. Groups II and III basestocks are more expensive to produce than Group I basestocks, and account for about 20 percent of all basestocks.

Group II and III basestocks may be "conventional" or "unconventional." Generally, "unconventional" basestocks are mineral oils with unusually high viscosity indices and unusually low volatilities. Low severity hydroprocessing and solvent refined Group II and III solvent refined mineral basestocks are "conventional." Compared to Group I solvent refined oils, severely hydroprocessed Group II and III oils offer lower volatility, and when properly additized, greater thermal and oxidative stability and lower pour points.

Group IV basestocks consists of polyalphaolefins. Group IV basestocks offer superior volatility, thermal stability, oxidative stability and pour point characteristics to those of the Group II and III oils with less reliance on additives. Currently, Group IV basestocks, the PAOs, make up about 3 percent of the base oil market. Group V includes all other basestocks not included in Groups I, II, III and IV. Substituted styrene dimers are Group V basestocks.

The basestock of the invention comprises (i) from about 10 weight % to about 78 weight %, alternatively from about 35 weight % to about 62 weight %, alternatively from about 40 weight % to about 50 weight % fully hydrogenated alpha-substituted styrene linear dimer; (ii) from about 10 weight % to about 60 weight %, alternatively from about 32 weight % to about 53 weight %, alternatively from about 38 weight % to about 48 weight % partially hydrogenated mono-aromatic alpha-substituted styrene linear dimer; and (iii) from about 0 weight % to about 30 weight %, alternatively from about 3 weight % to about 10 weight %, alternatively from about 7 weight % to about 9 weight % partially hydrogenated di-aromatic alpha-substituted styrene linear dimer, wherein the weight % is based on the total of (i), (ii) and (iii) and is determined by area percentages measured by gas chromatography analysis. However, area %=weight % for closely relate compounds such as these.

In one embodiment, the fully hydrogenated alpha-substituted styrene linear dimer comprises 2,4-bis-cyclohexyl-2-methylpentane. Conveniently, the fully hydrogenated alpha-substituted styrene linear dimer comprises greater than 90 weight %, such as greater than 95 weight %, for example greater than 99 weight %, 2,4-bis-cyclohexyl-2-methylpentane.

In one embodiment, the partially hydrogenated mono-aromatic alpha-substituted styrene linear dimer comprises 2-phenyl-4-cyclohexyl-2-methylpentane and 2-cyclohexyl-4-phenyl-2-methylpentane. Conveniently, the partially hydrogenated mono-aromatic alpha-substituted styrene linear dimer comprises greater than 90 weight %, such as greater than 95 weight %, for example greater than 99 weight %, 2-phenyl-4-cyclohexyl-2-methylpentane and 2-cyclohexyl-4-phenyl-2-methylpentane.

In one embodiment, the partially hydrogenated di-aromatic alpha-substituted styrene linear dimer comprises 2,4-diphenyl-2-methylpentane. Conveniently, the partially hydrogenated di-aromatic alpha-substituted styrene linear dimer comprises greater than 90 weight %, such as greater than 95 weight %, for example greater than 99 weight %, 2,4-diphenyl-2-methylpentane.

A typical basestock according to the invention comprises (i) from about 35 weight % to about 65 weight % 2,4-bis-cyclohexyl-2-methylpentane; (ii) from about 30 weight % to about 55 weight % 2-phenyl-4-cyclohexyl-2-methylpentane and 2-cyclohexyl-4-phenyl-2-methylpentane; and (iii) from about 5 weight % to about 15 weight % 2,4-diphenyl-2-methylpentane.

Generally, the basestock of the invention has a low temperature dynamic viscosity at −30° C. of from about 2600 cP to about 22700 cP, such as from about 4500 cP to about 11000 cP, alternatively from about 5500 cP to about 6500 cP, for example about 6300 cP.

Generally, the basestock of the invention has a traction coefficient of from about 0.055 to about 0.090, such as from about 0.060 to about 0.075, alternatively from about 0.065 to about 0.075, for example from about 0.067 to about 0.073.

Substituted Styrene

As shown below as structure IX, the substituted styrene monomer used to produce the basestock of the invention may be substituted at the alpha position with $R_1$ or the beta position with $R_2$ and dimerized followed by hydrogenation as discussed above. $R_1$ and $R_2$ are either hydrogen or an alkyl group, and in one embodiment $R_1$ and $R_2$ are not both alkyl groups simultaneously. $R_1$ and $R_2$ may each be an alkyl group having from one to about 20 carbon atoms, alternatively from one to about 10 carbon atoms, alternatively from one to about five carbon atoms, and alternatively one carbon atom.

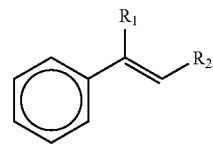

(IX)

Preparation of the Basestock Compositions

Preparation of the present basestock is conveniently achieved by a process comprising (i) reacting a feed stream comprising from about 96 weight % to about 98 weight % substituted styrene, from about 1 weight % to about 2 weight % of an alcohol, and from about 1 weight % to about 2 weight % dimerization catalyst, in the presence of a solvent, wherein the weight % is based on the total weight of the substituted styrene, alcohol, and dimerization catalyst, to form a crude slurry of dimerized substituted styrene; and (ii) partially hydrogenating the dimerized substituted styrene with hydrogen over a Group VIII catalyst. Alcohols, such as ethanol and others known to those skilled in the art may be used. Solvents, including pentane, heptane, and other solvents known to those skilled in the art may be used. Preferred solvents also provide some degree of temperature control. Catalysts suitable for the dimerization process include, but are not limited to, ion exchange resins, such as Amberlyst 15. A catalyst suitable for the partial hydrogenation step includes a nickel catalyst, such as G-49D, available from Sud-Chemie.

Conveniently, the dimerization step is conducted at a temperature of from about 50° C. to about 65° C., such as from about 55° C. to about 60° C. The partial hydrogenation step is conveniently conducted at a temperature of from about 150° C. to about 220° C., such as from about 175° C. to about 200° C., and a pressure of from about 250 psig to about 375 psig (1825 kPa to 2687 kPa), such as from about 275 psig to about 350 psig (1997 kPa to 2514 kPa), for example from about 300 psig to about 325 psig (2170 kPa to 2343 kPa).

Typically, between steps (i) and (ii), the process further comprises filtering the dimerization catalyst from the crude slurry of dimerized substituted styrene to obtain a crude substituted styrene linear dimer and stripping the crude substituted styrene linear dimer to form a purified substituted styrene linear dimer by removal of unreacted substituted styrene monomer, solvent and any other volatile compounds. Conveniently, the stripping step is conducted at a temperature of from about 150° C. to about 220° C., such as from about 175° C. to about 200° C.

Following step (ii), the composition comprising the fully hydrogenated substituted styrene linear dimer and the partially hydrogenated substituted styrene linear dimer may be filtered to remove the Group VIII catalyst.

Process Configurations

FIG. 1 discloses one embodiment of a process for producing partially-hydrogenated substituted styrene linear dimers. A feed stream 1 containing substituted styrene monomer, alcohol, and dimerization catalyst, and solvent stream 2, are fed into dimerization reactor 3. The dimerization product stream 4 is fed into filtration device 5, where the dimerization catalyst is removed via catalyst removal stream 6, and a filtered product stream 7 is fed into distillation column 8. Waste products, i.e., high boiling materials, are removed from distillation column 8 via waste stream 9 and the unreacted substituted styrene monomer and solvent are recycled via recycle stream 11. The distilled substituted styrene linear dimer is removed via distillation product stream 10 and is fed into hydrogenation reactor 14. Catalyst and hydrogen are fed into hydrogenation reactor 14 via catalyst stream 12 and hydrogen stream 13, respectively. The hydrogenation product is removed via hydrogenation product stream 15, which is fed into filtration device 16. Catalyst is removed from filtration device 16 via catalyst removal stream 17. Partially and fully hydrogenated substituted styrene linear dimers are removed from filtration device 16 via hydrogenated product stream 18.

Additives

In one embodiment, the basestock of the invention is used with additional lubricant additives in effective amounts typically used in lubricant compositions, such as, for example, polar and/or non-polar lubricant basestocks. The effective amounts of the additives used in the lubricant composition can be readily determined by conventional methods known to one of ordinary skill in the art. Generally, lubricant composition will comprise from about 80 weight % to about 99 weight % of the basestock of the invention and from about 1 weight % to about 20 weight % of at least one additive, wherein the weight % is based on the total weight of the lubricant. Suitable additives include, but are not limited to, oxidation inhibitors, metallic and non-metallic dispersants, metallic and non-metallic detergents, corrosion and rust inhibitors, metal deactivators, anti-wear agents (metallic and non-metallic, phosphorus-containing and non-phosphorus, sulfur-containing and non-sulfur types), extreme pressure additives (metallic and non-metallic, phosphorus-containing and non-phosphorus, sulfur-containing and non-sulfur types), anti-seizure agents, pour point depressants, wax modifiers, viscosity modifiers, seal compatibility agents, friction modifiers, lubricity agents, anti-staining agents, chromophoric agents, defoamants, demulsifiers, and others.

For a review of many commonly used additives see Klamann in Lubricants and Related Products, Verlag Chemie, Deerfield Beach, Fla.; ISBN 0-89573-177-0, which discusses a number of the lubricant additives identified above. Reference is also made to "Lubricant Additives" by M. W. Ranney, published by Noyes Data Corporation of Parkridge, N.J. (1973).

EXAMPLES

Test Methods

Kinematic viscosity was measured by ASTM D-445-3 (40° C.) and ASTM D-445-5 (100° C.).

Viscosity index was measured by ASTM-D2270.

Low temperature dynamic viscosity was measured by ASTM D-5293.

The traction coefficient was determined by the following procedure. A Mini Traction Machine (MTM) Traction Measurement System available from PCS Instruments was used to measure the traction coefficient of the fluids. The ¾-inch ball was used to measure and calculate the traction coefficient at the indicated pressures, temperatures, and slip percentage in the data tables below.

Gas Chromatography (GC) was performed to determine product compositions and was performed by a process known to those skilled in the art with a Hewlett Packard 5890 Gas Chromatograph, comprising a split/splitless injector port and FID detector, using a Restek MTX-1 capillary GC column, with a 15 m length, 0.28 mm ID and 0.25 μm film thickness. The tests were run under an injector temperature of 325° C. and a detector temperature of 375° C., with a 60:1 split ratio. The oven temperature was 80° C. initially for 2 minutes and was ramped up at 25° C./min. to 360° C. The temperature was held at 360° C. for 4.8 minutes. HP Chemstation software was used to integrate the signal and the composition was determined by GC peak area %.

Infrared Spectroscopy (IR) was performed to determine product compositions and was performed by a process known to those skilled in the art. Standard IR spectra for 2,4,-diphenyl-4-methyl-1-pentene (unhydrogenated alpha-methylstyrene dimer) and 1,1'-(1,1,3-trimethyl-1,3-prapoanediyl)bis-cyclohexane (fully hydrogenated alpha-methylstyrene dimer), available from Aldrich, were used for IR correlation.

Examples 1-9

Mixtures Comprising Hydrogenated AMS Dimerization 400 lbs. (181.6 kg) of n-pentane were charged to a clean, dry, and pressure-checked reactor. The reactor was set for total reflux. 15.2 lbs. (6.9 kg) of ethyl alcohol were charged to the reactor. 15.2 lbs. (6.9 kg) of Amberlyst 15, available from Rohm and Haas, Philadelphia, Pa., were charged to the reactor, by forming a slurry of the Amberlyst 15 resin and the n-pentane. Once all of the Amberlyst 15 resin was charged, the remainder of the n-pentane was charged to the reactor to total 525.7 lbs. (238.7 kg) of n-pentane. The weight and volume of the chemicals charged to the reactor are shown in Table 1 below.

After all of the n-pentane, ethyl alcohol, and Amberlyst 15 resin was added to the reactor, the reactor was sealed, evacuated and purged three times with nitrogen to 20 psig (239 kPa) to inert the vessel. The reactor was sealed at 0 psig.

The reactor was then heated to 55° C. with mixing and the pressure inside the reactor rose to 12-15 psig (184 kPa to 204 kPa). Once a temperature of 55° C. was reached, the alpha-methylstyrene, available from Sunoco, Philadelphia, Pa., was added at a rate of 3.16 lbs./min. (1.4 kg/min) over a 4 hour period. The reactor temperature was held at around 55° C. during the entire reaction by modifying the alpha-methylstyrene feed rate as needed to control the temperature.

The reactor pot temperature was maintained at 55° C. for 2 hours after completion of the alpha-methylstyrene addition. A 2-oz. sample of the reaction product was taken for GC analysis. The reactor pot temperature was maintained at 55° C. during analysis.

After the reaction was completed, the reactor product was cooled to below 25° C. and the Amberlyst 15 resin was removed by filtration.

TABLE 1

Weight and Volume of Chemicals to Charge - Dimerization Feed

| Chemical Name | Pounds to Charge | Gallons to Charge |
| --- | --- | --- |
| a-Methylstyrene | 758.5 (344.3 kg) | 100.0 (379 l) |
| Amberlyst 15 | 15.2 (6.9 kg) | 1.3-1.7 (4.9-6.4 l) |
| Ethyl Alcohol | 15.2 (6.9 kg) | 2.3 (8.7 l) |
| n-Pentane | 525.7 (181.6 kg) | 100.0 (379 l) |

Pre-Strip

The reactor was heated and the pressure reduced slowly to distill off the n-pentane and any unreacted alpha-methylstyrene. Reactor pot temperature did not exceed 190° C. and the pressure did not drop below 20 mm Hg (2.7 kPa) during the pre-strip. A 2-oz. sample was pulled from the reactor pot every 2 hours during the pre-strip until the level of n-pentane in the reactor pot was below 1.0%, as determined by GC analysis.

When the pre-strip was complete, the pressure was increased to 0 psig (101 kPa) by introducing into the reactor nitrogen. The reactor was cooled to below 30° C. The crude alpha-methylstyrene linear dimer remained in the reactor under nitrogen until hydrogenation was performed.

Distillation/Stripping

The crude alpha-methylstyrene linear dimer was distilled. The unreacted monomer and impurities (lights) were removed by distillation. The removal of the lights was complete when distillate samples contained less than 1.0 weight % solvent and unreacted monomer. The distilled dimer was collected in 1-liter fractions until the % trimers in the fractions was greater than 1.0 weight %. The lights and the remaining bottoms material were discarded. The purified linear dimers were hydrogenated as described below.

Hydrogenation

Batches of purified linear dimer of alpha-methylstyrene were hydrogenated in a 2-gallon Parr reactor. The conditions of the hydrogenation were: 200° C. until about 80% of the purified alpha-methylstyrene linear dimer was partially hydrogenated; 350 psig (2170 kPa) hydrogen; 1.0 weight % G-49D nickel catalyst; 750 RPM. This procedure was repeated until all of the purified alpha-methylstyrene linear dimer formed in the dimerization process was partially hydrogenated.

5000 grams of filtered, fully prestripped hydrogenation feed alpha-methylstyrene linear dimer (approx. 1.3 gallons) was charged to the 2-gallon Parr reactor set-up to do slurry hydrogenations.

50 grams of G-49D Nickel catalyst was charged to the reactor. The catalyst was slurried in the hydrogenation feed and blown into the reactor from a pressurized carboy. The weight and volume of chemicals charged to the reactor are shown in Table 2 below.

TABLE 2

Weight and Volume of Chemicals to Charge - Hydrogenation Feed

| Chemical Name | Grams to Charge | Gallons to Charge |
| --- | --- | --- |
| Purified AMS dimer | 5000 | 1.3 (4.9 l) |
| G-49D Nickel catalyst | 50 | 0.2 (0.8 l) |
| Hydrogen | 91 | Not applicable |

The reactor was vented and purged 3 times at 80 psig (653 kPa) with nitrogen, and the reactor was pressurized at 80 psig (653 kPa) to test for any leaks. After determining that the reactor was leak-tight, the reactor was vented to 5 psig (135 kPa) and sealed.

The reactor was filled to 350 psig (2170 kPa) with hydrogen. The hydrogen feed line was left open, with the regulator set at 350 psig (2170 kPa). The mixer was turned on to 750 RPM, and the reactor was heated to 200° C. The reactor temperature was maintained at 200° C. A 10 cc sample was withdrawn every 10 minutes and an IR was performed on each sample to determine the level of hydrogenation. The hydrogen flow was stopped once the IR correlation of hydrogen saturation reached the desired level.

If the reaction stopped (no more hydrogen was being consumed) before completion, the hydrogen was turned off and the reactor was cooled to below 40° C. The hydrogen was vented off slowly with the mixer on at 300 RPM. The reactor was vented and purged 5 times with nitrogen. Using 50 psig (446 kPa) nitrogen, 4 lbs. (1.8 kg) of partially reacted slurry were pressurized out from the reactor bottom valve into the Mix Carboy. 50 grams of fresh G-49D Nickel catalyst were added and mixed. The partially reacted slurry was blown back into the reactor, and the hydrogenation procedure was repeated until the desired IR correlation of hydrogen saturation was reached.

When the reaction was completed, the reactor was cooled to below 40° C. and a 1-oz. sample was pulled.

The hydrogenated alpha-methylstyrene linear dimer slurry was filtered.

The kinematic viscosity, low temperature dynamic viscosity, and traction coefficient results for Examples 1 through 9, along with their respective compositions, are shown in Table 3 below.

TABLE 3

Compositions and Properties of Reactant Products

| | Example # | | | | | | | | |
|---|---|---|---|---|---|---|---|---|---|
| | 1 | 2 | 3 | 4 | 5 | 6 | 7 | 8 | 9 |
| AMS Dimer Basestock Composition (weight %) | | | | | | | | | |
| Fully Hydrogenated | 99.3 | 87.7 | 80.4 | 70.4 | 61.6 | 42.7 | 35.4 | 13.4 | 49.0 |
| Partially Hydrogenated Mono-Aromatic | 0.3 | 11.5 | 17.4 | 25.5 | 32.7 | 47.9 | 53.8 | 58.1 | 34.2 |
| Partially Hydrogenated Di-Aromatic | 0.0 | 0.0 | 1.4 | 3.3 | 5.1 | 8.7 | 10.1 | 28.0 | 9.4 |
| Kinematic Viscosity | | | | | | | | | |
| @ 40° C., cSt | 20.36 | 19.80 | 17.92 | 15.96 | 14.35 | 11.97 | 11.21 | 9.04 | 12.73 |
| @ 100° C., cSt | 3.60 | 3.56 | 3.42 | 3.28 | 3.09 | 2.76 | 2.66 | 2.33 | 2.85 |
| VI | 14 | 19 | 33 | 51 | 54 | 52 | 55 | 54 | 49 |
| Low Temperature Dynamic Viscosity | | | | | | | | | |
| @ −30° C., cP | 37700 | 34200 | 22700 | 14000 | 10600 | 6000 | 4800 | 2600 | 6239 |
| @ −35° C., cP | 99300 | 95500 | 67300 | 40500 | 29700 | 15600 | 13200 | 6700 | 16495 |
| Traction Coefficient | | | | | | | | | |
| @ 120° C.; 1.25 GPa; 2.0 m/s; 5% Slip | 0.0828 | 0.0832 | 0.0804 | 0.0759 | 0.0729 | 0.0668 | 0.0653 | 0.0557 | 0.069 estimated |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A process of producing a basestock, the process comprising:
   (i) reacting a feed stream comprising from about 96 weight % to about 98 weight % substituted styrene, from about 1 weight % to about 2 weight % alcohol, and from about 1 weight % to about 2 weight % dimerization catalyst, in the presence of a solvent, wherein the weight % is based on the total weight of the substituted styrene, alcohol, and dimerization catalyst, to form a crude slurry of dimerized substituted styrene; and
   (ii) partially hydrogenating the dimerized substituted styrene with hydrogen over a Group VIII catalyst to form a basestock comprising:
      (a) from about 10 weight % to 78 weight % fully hydrogenated substituted styrene linear dimer;
      (b) from about 10 weight % to about 60 weight % partially hydrogenated mono-aromatic substituted styrene linear dimer; and
      (c) from about 0 weight % to about 30 weight % partially hydrogenated di-aromatic substituted styrene linear dimer,
   wherein the weight % is based on the total of (a), (b) and (c).

2. The process of claim 1 wherein said substituted styrene has the following formula IX:

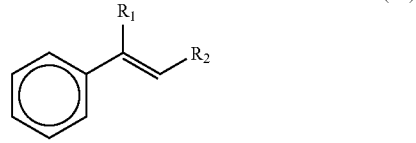

(IX)

wherein each of $R_1$ and $R_2$ is independently an alkyl group having 1 to 20 carbon atoms.

3. The process of claim 2 wherein each of $R_1$ and $R_2$ is methyl.

4. The process of claim 1 further comprising filtering the crude slurry of dimerized substituted styrene to form a crude substituted styrene linear dimer.

5. The process of claim 4 further comprising stripping solvent and unreacted substituted styrene at reduced pressure from the crude substituted styrene linear dimer to form a purified substituted styrene linear dimer.

6. The process of claim 5 wherein the stripping occurs at a temperature from about 150° C. to about 220° C.

7. The process of claim 1 further comprising filtering the basestock to remove the Group VIII catalyst.

8. The process of claim 1 wherein the dimerization catalyst is an ion exchange resin.

9. The process of claim 1 wherein the dimerization occurs at a temperature from about 50° C. to about 65° C.

10. The process of claim 1 wherein the partial hydrogenation occurs at a temperature from about 150° C. to about 220° C.

11. The process of claim 1 wherein the partial hydrogenation occurs at a pressure from about 250 psig to about 375 psig (1825 kPa to 2687 kPa).

12. The process of claim 1 wherein the Group VIII catalyst comprises nickel.

13. The process of claim 1 wherein the fully hydrogenated substituted styrene linear dimer comprises 2,4-bis-cyclohexyl-2-methylpentane.

14. The process of claim 1 wherein the partially hydrogenated mono-aromatic substituted styrene linear dimer comprises 2-phenyl-4-cyclohexyl-2-methylpentane and 2-cyclohexyl-4-phenyl-2-methylpentane.

15. The process of claim 1 wherein the partially hydrogenated di-aromatic substituted styrene linear dimer comprises 2,4-diphenyl-2-methylpentane.

16. The process of claim 1, wherein the basestock has a low temperature dynamic viscosity at −30° C. of from about 2600 cP to about 22700 cP.

17. The process of claim 1 wherein the basestock has a traction coefficient from about 0.060 to about 0.075.

18. The process of claim 1, wherein the basestock has a Viscosity Index of about 49 to about 55.

19. A process of producing a basestock, the process comprising:
   (i) reacting a feed stream comprising from about 96 weight % to about 98 weight % substituted styrene, from about 1 weight % to about 2 weight % alcohol, and from about 1 weight % to about 2 weight % dimerization catalyst, in the presence of a solvent, wherein the weight % is based on the total weight of the substituted styrene, alcohol, and dimerization catalyst, to form a crude slurry of dimerized substituted styrene; and
   (ii) partially hydrogenating the dimerized substituted styrene with hydrogen over a Group VIII catalyst to form a basestock comprising:
      (a) from about 35 weight % to about 62 weight % fully hydrogenated substituted styrene linear dimer;
      (b) from about 32 weight % to about 53 weight % partially hydrogenated mono-aromatic substituted styrene linear dimer; and
      (c) from about 3 weight % to about 10 weight % partially hydrogenated di-aromatic substituted styrene linear dimer, wherein the weight % is based on the total of (a), (b) and (c).

20. The process of claim 19 wherein said substituted styrene has the following formula IX:

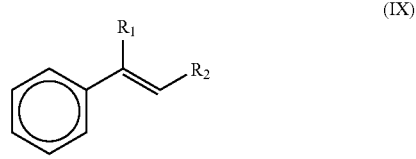

wherein each of $R_1$ and $R_2$ is independently an alkyl group having 1 to 20 carbon atoms.

21. The process of claim 19 wherein each of $R_1$ and $R_2$ is methyl.

22. The process of claim 19 wherein the dimerization catalyst is an ion exchange resin.

23. The process of claim 19 wherein the dimerization occurs at a temperature from about 50° C. to about 65° C.

24. The process of claim 19 wherein the partial hydrogenation occurs at a temperature from about 150° C. to about 220° C. and a pressure from about 250 psig to about 375 psig (1825 kPa to 2687 kPa).

25. The process of claim 19 wherein the Group VIII catalyst comprises nickel.

26. The process of claim 19, wherein the basestock has a low temperature dynamic viscosity at −30° C. of from about 2600 cP to about 22700 cP.

27. The process of claim 19 wherein the basestock has a traction coefficient from about 0.060 to about 0.075.

28. The process of claim 19, wherein the basestock has a Viscosity Index of about 49 to about 55.

* * * * *

UNITED STATES PATENT AND TRADEMARK OFFICE
CERTIFICATE OF CORRECTION

PATENT NO. : 7,629,303 B2  Page 1 of 1
APPLICATION NO. : 11/205679
DATED : December 8, 2009
INVENTOR(S) : Hagemeister et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1148 days.

Signed and Sealed this

Second Day of November, 2010

David J. Kappos
*Director of the United States Patent and Trademark Office*